US006964946B1

(12) United States Patent
Gutierrez-Rocca et al.

(10) Patent No.: US 6,964,946 B1
(45) Date of Patent: Nov. 15, 2005

(54) ORAL PHARMACEUTICAL COMPOSITIONS CONTAINING TAXANES AND METHODS OF TREATMENT EMPLOYING THE SAME

(75) Inventors: Jose C. Gutierrez-Rocca, Miami, FL (US); Janice L. Cacace, Miami, FL (US); Sami Selim, Irvine, CA (US); Robert Testman, Corona, CA (US); J. Michael Rutledge, Riverdale, NY (US)

(73) Assignee: Baker Norton Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 09/055,818

(22) Filed: Apr. 6, 1998

Related U.S. Application Data

(63) Continuation-in-part of application No. 08/863,513, filed on May 27, 1997, now abandoned, which is a continuation-in-part of application No. 08/733,142, filed on Oct. 16, 1996, now Pat. No. 6,245,805, which is a continuation-in-part of application No. 08/608,776, filed on Feb. 29, 1996, now Pat. No. 5,968,972.

(60) Provisional application No. 60/007,071, filed on Oct. 26, 1995.

(51) Int. Cl.[7] .......................................... A61K 31/337
(52) U.S. Cl. ...................................... 514/11; 514/449
(58) Field of Search ....................................... 514/449

(56) References Cited

U.S. PATENT DOCUMENTS

| | | | | |
|---|---|---|---|---|
| 4,960,790 A | 10/1990 | Stella et al. | ................ | 514/449 |
| 5,403,858 A | 4/1995 | Bastard et al. | ............... | 514/449 |
| 5,438,072 A | 8/1995 | Bobee et al. | ................ | 514/449 |
| 5,504,102 A | 4/1996 | Agharkar et al. | ........... | 514/449 |
| 5,565,478 A | 10/1996 | Kohn et al. | ................. | 514/359 |
| 5,610,173 A | 3/1997 | Schwartz et al. | ........... | 514/378 |
| 5,616,330 A | 4/1997 | Kaufman et al. | ........... | 424/400 |
| 5,646,176 A | 7/1997 | Golik et al. | ................ | 514/444 |
| 5,665,386 A | 9/1997 | Benet et al. | ................ | 424/451 |
| 5,681,846 A | 10/1997 | Trissel | ........................ | 514/449 |
| 5,716,928 A | 2/1998 | Benet et al. | .................. | 514/11 |
| 5,877,205 A | 3/1999 | Andersson | ................... | 514/449 |
| 5,972,992 A | 10/1999 | Carver et al. | ............... | 514/449 |
| 6,004,927 A | 12/1999 | Benet et al. | ..................... | 514/9 |
| 6,028,054 A | 2/2000 | Benet et al. | ..................... | 514/9 |
| 6,096,331 A | 8/2000 | Desai et al. | ................ | 424/422 |
| 6,245,805 B1 * | 6/2001 | Broder et al. | ............... | 514/449 |
| 6,458,373 B1 * | 10/2002 | Lambert et al. | ............ | 424/405 |
| 6,610,735 B2 | 8/2003 | Broder et al. | ............... | 514/449 |
| 2001/0029264 A1 | 10/2001 | McChesney-Harris | ...... | 514/449 |
| 2002/0025337 A1 | 2/2002 | Illum et al. | | |

FOREIGN PATENT DOCUMENTS

| | | |
|---|---|---|
| WO | WO 95/20980 | 8/1995 |
| WO | WO 97/15269 | 5/1997 |
| WO | WO97/23208 | 7/1997 |
| WO | 98/30205 | 7/1998 |
| WO | WO 98/57630 | 12/1998 |
| WO | WO 99/06024 | 2/1999 |
| WO | WO 99/12570 | 3/1999 |
| WO | 99/45918 | 9/1999 |
| WO | WO 99/49848 | 10/1999 |

OTHER PUBLICATIONS

Lum et al., Drug Resistance in Clin. Onc. and Hematology, vol. 9, No. 2, pp. 319-336 (1995).
Fisher et al., Proc. of ASCO, vol. 13, Abstract 369, p. 144 (1994).
Tarr, B.D. et al.; Pharmaceutical Research, vol. 4:2, pp. 162-165 (1987).
Prankerd, R. J. et al.; J. Parenteral Science and Technology, 44:3, pp. 139-149 (1990).
Adams, J. et al.; J. National Cancer Institute Monographs, 15, pp. 141-147 (1993).
Wheeler, J. et al.; J. Pharmaceutical Sciences, 83:11, pp. 1558-1564 (1994).
Wu, S. et al.; Pharmaceutical Research, vol. 11:10, p. S-149, PT6074, (1994) Supp.

* cited by examiner

*Primary Examiner*—Richard L. Raymond
(74) *Attorney, Agent, or Firm*—Lerner, David, Littenberg, Krumholz & Mentlik, LLP

(57) ABSTRACT

Pharmaceutical compositions for oral administration to mammalian subjects comprise a taxane or taxane derivative (e.g., paclitaxel or docetaxel) as active ingredient and a vehicle comprising at least 30% by weight of a carrier for the taxane, said carrier having an HLB value of at least about 10. The compositions may also comprise 0–70% of a viscosity-reducing co-solubilizer. The compositions may be incorporated into conventional oral pharmaceutical dosage forms, or can be in the form of a two-part medicament wherein the first part includes the taxane in a solubilizing vehicle and the second part comprises a carrier for the taxane to promote oral absorption. Methods of treatment of taxane-responsive disease conditions employing the novel compositions are also disclosed, whereby the compositions can be administered alone or in association with an oral bioavailability enhancing agent.

161 Claims, No Drawings

ORAL PHARMACEUTICAL COMPOSITIONS CONTAINING TAXANES AND METHODS OF TREATMENT EMPLOYING THE SAME

CROSS-REFERENCE TO RELATED APPLICATIONS

This application is a continuation-in-part of application Ser. No. 08/863,513, filed May 27, 1997, abandoned, which is a continuation-in-part of application Ser. No. 08/733,142, filed Oct. 16, 1996, now U.S. Pat. No. 6,245,805, which is a continuation-in-part of application Ser. No. 08/608,776, filed Feb. 29, 1996, now U.S. Pat. No. 5,968,972, which claims the priority of provisional application Ser. No. 60/007,071, filed Oct. 26, 1995.

BACKGROUND OF THE INVENTION

1. Field of the Invention

The invention relates to compositions for orally administering paclitaxel and related taxanes to human patients, and methods of treatment employing such compositions.

2. Description of the Prior Art

Many valuable pharmacologically active compounds cannot be effectively administered by the oral route to human patients because of poor or inconsistent systemic absorption from the gastrointestinal tract. These pharmaceutical agents are, therefore, generally administered via intravenous routes, requiring intervention by a physician or other health care professional, entailing considerable discomfort and potential local trauma to the patient and even requiring administration in a hospital setting with surgical access in the case of certain IV infusions.

One of the important classes of cytotoxic agents which are not normally bioavailable when administered orally to humans are the taxanes, which include paclitaxel, its derivatives and analogs. Paclitaxel (currently marketed as TAXOL® by Bristol-Myers Squibb Oncology Division) is a natural diterpene product isolated from the Pacific yew tree (*Taxus brevifolia*). It is a member of the taxane family of terpenes. It was first isolated in 1971 by Wani et al. (*J. Am. Chem. Soc.,* 93:2325, 1971), who characterized its structure by chemical and X-ray crystallographic methods. One mechanism for its activity relates to paclitaxel's capacity to bind tubulin, thereby inhibiting cancer cell growth. Schiff et al., *Proc. Natl. Acad. Sci. USA,* 77:1561–1565 (1980); Schiff et al., *Nature,* 277:665–667 (1979); Kumar, *J. Biol. Chem.,* 256: 10435–10441 (1981).

Paclitaxel has been approved for clinical use in the treatment of refractory ovarian cancer in the United States (Markman et al., *Yale Journal of Biology and Medicine,* 64:583, 1991; McGuire et al., *Ann. Intern. Med.,* 111:273, 1989). It is effective for chemotherapy for several types of neoplasms including breast (Holmes et al., *J. Nat. Cancer Inst.,* 83:1797, 1991) and has been approved for treatment of breast cancer as well. It is a potential candidate for treatment of neoplasms in the skin (Einzig et al., *Proc. Am. Soc. Clin. Oncol.,* 20:46), lung cancer and head and neck carcinomas (Forastire et al. *Sem. Oncol.,* 20:56, 1990). The compound also shows potential for the treatment of polycystic kidney disease (Woo et al, *Nature,* 368:750, 1994) and malaria.

Paclitaxel is only slightly soluble in water and this has created significant problems in developing suitable injectable and infusion formulations useful for anticancer chemotherapy. Some formulations of paclitaxel for IV infusion have been developed utilizing CREMOPHOR EL™ (polyethoxylated castor oil) as the drug carrier because of paclitaxel's aqueous insolubility. For example, paclitaxel used in clinical testing under the aegis of the NCI has been formulated in 50% CREMOPHOR EL™ and 50% dehydrated alcohol. CREMOPHOR EL™ however, when administered intravenously, is itself toxic and produces vasodilation, labored breathing, lethargy, hypotension and death in dogs. It is also believed to be at least partially responsible for the allergic-type reactions observed during paclitaxel administration, although there is some evidence that paclitaxel may itself provoke acute reactions even in the absence of Cremophor.

In an attempt to increase paclitaxel's solubility and to develop more safe clinical formulations, studies have been directed to synthesizing paclitaxel analogs where the 2' and/or 7-position is derivatized with groups that would enhance water solubility. These efforts have yielded prodrug compounds that are more water soluble than the parent compound and that display the cytotoxic properties upon activation. One important group of such prodrugs includes the 2'-onium salts of paclitaxel and docetaxel, particularly the 2'-methylpyridinium mesylate (2'-MPM) salts.

Paclitaxel is very poorly absorbed when administered orally (less than 1%); see Eiseman et al., *Second NCI Workshop on Taxol and Taxus* (September 1992); Suffness et al. in *Taxol Science and Applications* (CRC Press 1995). Eiseman et al. indicate that paclitaxel has a bioavailability of 0% upon oral administration, and Suffness et al. report that oral dosing with paclitaxel did not seem possible since no evidence of antitumor activity was found on oral administration up to 160 mg/kg/day. For this reason, paclitaxel has not been administered orally to human patients in the prior art, and certainly not in the course of treating paclitaxel-responsive diseases.

Docetaxel (N-debenzoyl-N-tert-butoxycarbonyl-10-deacetyl paclitaxel) has become commercially available as TAXOTERE® (Rhone-Poulenc-Rorer S. A.) in parenteral form for the treatment of breast cancer. To dates no reference has been made in the scientific literature to oral absorption of docetaxel in animals or patients.

It has been speculated that, in some cases, the poor or non-existent bioavailability of a drug such as paclitaxel after oral administration is a result of the activity of a multidrug transporter, a membrane-bound P-glycoprotein, which functions as an energy-dependent transport or efflux pump to decrease intracellular accumulation of drug by extruding xenobiotics from the cell. This P-glycoprotein has been identified in normal tissues of secretory endothelium, such as the biliary lining, brush border of the proximal tubule in the kidney and luminal surface of the intestine, and vascular endothelial cells lining the blood brain barrier, placenta and testis.

It is believed that the P-glycoprotein efflux pump prevents certain pharmaceutical compounds from transversing the mucosal cells of the small intestine and, therefore, from being absorbed into the systemic circulation. A number of known non-cytotoxic pharmacological agents have been shown to inhibit P-glycoprotein, including cyclosporin A (also known as cyclosporine), verapamil, tamoxifen, quinidine and phenothiazines, among others. Many of these studies were aimed at achieving greater accumulation of intravenously administered cytotoxic drugs inside tumor cells. In fact, clinical trials have been conducted to study the effects of cyclosporine on the pharmacokinetics and toxicities of paclitaxel (Fisher et al., *Proc. Am. Soc. Clin. Oncol.,* 13: 143, 1994); doxorubicin (Bartlett et al., *J. Clin. One.* 12:835–842, 1994); and etoposide (Lum et al., *J. Clin. One.* 10:1635–42, 1992), all of which are anti-cancer agents known to be subject to multidrug resistance (MDR). These trials showed that patients receiving intravenous cyclosporine prior to or together with the anti-cancer drugs had higher blood levels of those drugs, presumably through reduced body clearance, and exhibited the expected toxicity at substantially lower dosage levels. These findings tended to indicate that the concomitant administration of cyclosporine suppressed the MDR action of P-glycoprotein, enabling larger intracellular accumulations of the therapeutic agents. For a general discussion of the pharmacologic implications for the clinical use of P-glycoprotein inhibitors, see Lum et al., *Drug Resist. Clin. One. Hemat.,* 9: 319–336 (1995); Schinkel et al., *Eur. J. Cancer,* 31A: 1295–1298 (1995).

In the aforedescribed studies relating to the use of cyclosporine to increase the blood levels of pharmaceutical agents, the active anti-tumor agents and the cyclosporine were administered intravenously. No suggestion was made in these publications that cyclosporine could be orally administered to substantially increase the bioavailability of orally administered anti-cancer drugs and other pharmaceutical agents which are themselves poorly absorbed from the gut without producing highly toxic side effects. None of the published studies provided any regimen for implementing the effective oral administration to humans of poorly bioavailable drugs such as paclitaxel, e.g., indicating the respective dosage ranges and timing of administration for specific target drugs and bioavailability-enhancing agents are best suited for promoting oral absorption of each target drug or class of drugs.

In published PCT application WO 95/20980 (published Aug. 10, 1995) Benet et al. disclose a purported method for increasing the bioavilability of orally administered hydrophobic pharmaceutical compounds. This method comprises orally administering such compounds to the patient concurrently with a bioenhancer comprising an inhibitor of a cytochrome P450 3A enzyme or an inhibitor of P-glycoprotein-mediated membrane transport. Benet et al., however, provide virtually no means for identifying which bioavailability enhancing agents will improve the availability of specific "target" pharmaceutical compounds, nor do they indicate specific dosage amounts, schedules or regimens for administration of the enhancing or target agents. In fact, although the Benet et al. application lists dozens of potential enhancers (P450 3A inhibitors) and target drugs (P450 3A substrates), the only combination of enhancer and target agent supported by any experimental evidence in the application is ketoconazole as the enhancer and cyclosporin A as the target drug.

When describing the general characteristics of compounds which can be used as bioenhancers by reduction of P-glycoprotein transport activity, Benet et al. indicate that these are hydrophobic compounds which generally, but not necessarily, comprise two co-planar aromatic rings, a positively charged nitrogen group or a carbonyl group—a class that includes an enormous number of compounds, most of which would not provide the desired absorption enhancing activity in the case of specific target agents. Moreover, the classes of target agents disclosed by Benet et al. include the great majority of pharmaceutical agents listed in the *Physicians' Desk Reference*. These inclusion criteria are of no value to medical practitioners seeking safe, practical and effective methods of orally administering specific pharmaceutical agents.

In general, Benet et al. provides no teaching that could be followed by persons skilled in the medical and pharmaceutical arts to identify suitable bioenhancer/target drug combinations or to design specific treatment regimens and schedules which would render the target agents therapeutically effective upon oral administration to human patients. Benet et al. also provides no direction whatsoever regarding how paclitaxel and other taxanes might be administered orally to humans with therapeutic efficacy and acceptable toxicity.

In published PCT application WO 97/15269, which corresponds to U.S. patent application Ser. No. 08/733,142 (the grandparent of the present application) and which 10 is commonly owned with this application, it is disclosed that various therapeutically effective pharmaceutical "target agents" which exhibit poor oral bioavailability can be made bioavailable, providing therapeutic blood levels of the active agent, by oral co-administration of certain bioavailability enhancing agents. Preferred examples of such target agents disclosed in WO 97/15269 include the cyclosporins, e.g., cyclosporins A, D and G. Preferred examples of target agents include the taxane class of antineoplastic agents, particularly paclitaxel. Therapeutic regimens and dosage amounts for co-administration for target agents and enhancing agents are also disclosed. All of the disclosures of published application WO 97/15269 are incorporated herein by reference.

Neither commonly owned application WO 97/15269 nor any prior art disclosure, however, describes classes of oral formulations or compositions containing the active target agent, e.g., paclitaxel, which are particularly adapted for co-administration with an oral bioavailability enhancing agent to yield therapeutic blood levels of target agents heretofore considered unsuitable for oral administration.

SUMMARY OF THE INVENTION

The present invention relates to oral pharmaceutical compositions containing taxane antitumor agents, for example paclitaxel or docetaxel, which, when administered to a mammalian patient, preferably with co-administration of an oral bioavailability enhancing agent, enable sufficient absorption of the taxane agent from the gastrointestinal tract into the bloodstream to provide therapeutically significant blood levels of the active drug.

The compositions of the invention comprise a vehicle including a carrier in which the taxane agent is dissolved or dispersed. The vehicle may also include a viscosity-reducing co-solubilizer which renders the vehicle more flowable at body temperature or at least reduces the melting point of the vehicle below body temperature, and may also provide increased taxane solubility.

The carrier used in the novel compositions is preferably a non-ionic surface active agent (surfactant) or emusifier having a hydrophilic-lipophilic balance (HLB) value at least about 10. The viscosity-reducing co-solubilizer is selected from, e.g., organic solvents suitable for oral administration, vegetable oils, hydrogenated or polyoxyethylated castor oil, citrate esters and saturated polyglycolized glycerides. Certain saturated polyglycolized glycerides may also serve as carriers in the compositions of the invention.

The novel pharmaceutical compositions contain about 2–500 mg/ml or mg/g of taxane, and preferably about 2–50 mg/ml or mg/g of taxane. The therapeutically inactive vehicle comprises at least 30% by weight of carrier and about 0–70% of co-solubilizer, and may also contain conventional pharmaceutical additives and excipients such as flavoring and coloring agents and the like.

Another aspect of the invention pertains to methods of treatment of mammalian patients suffering from taxane-responsive disease conditions by the administration to such patients of oral pharmaceutical compositions in accordance with the invention, preferably with co-administration of an oral bioavailability enhancing agent.

DETAILED DESCRIPTION OF THE INVENTION

The oral pharmaceutical compositions of the invention contain at least two components: an active agent comprising a taxane, preferably the antitumor agent paclitaxel or docetaxel, and a therapeutically inactive vehicle comprising a pharmaceutically acceptable carrier for said taxane.

In order to produce compositions for oral administration that are liquid or at least flowable form at body temperature (about 37° C.), as generally required for oral bioavailability, it is required in some instances to add an additional component to the vehicle: a viscosity-reducing co-solubilizer which decreases the viscosity and increases the flowability of the vehicle at body temperature, and also may increase the amount of the active agent that can be dissolved or dispersed in the vehicle in comparison with the use of a carrier alone.

The novel compositions may comprise more than one taxane as active ingredient and more than one carrier and/or co-solubilizer as inactive vehicle components. The vehicle comprises at least 30% by weight of carrier, preferably 30–90% by weight. Preferred carriers for use in the invention are non-ionic surfactants or emulsifiers having HLB values at least about 10. It has been found that such non-ionic surfactants or emulsifiers are not only compatible carriers for the lipophilic taxanes (which are poorly soluble in water) but also promote absorption of the active ingredient from the gastrointestinal tract into the bloodstream.

Preferred carriers for use in the invention include, for example, Vitamin E TPGS (d-α-tocopheryl polyethylene glycol 1000 succinate, Eastman Chemical Co., Kingsport Tenn.); saturated polyglycolyzed glycerides such as GELUCIRE™ and LABRASOL™ products (Gattefossé Corp., Westwood, N.J.) which include glycerides of $C_8$–$C_{18}$ fatty acids; CREMOPHOR™ EL or RH40 modified castor oils (BASF, Mt. Olive, N.J.); MYRJ™ polyoxyethylated stearate esters (ICI Americas, Charlotte, N.C.); TWEEN™ (ICI Americas) and CRILLET™ (Croda Inc., Parsippany, N.J.) polyoxyethylated sorbitan esters; BRIJ™ polyoxyethylated fatty ethers (ICI Americas); CROVOL™ modified (polyethylene glycol) almond and corn oil glycerides (Croda Inc.); EMSORB™ sorbitan diisostearate esters (Henkel Corp., Ambler, Pa.); SOLUTOL™ polyoxyethylated hydroxystearates (BASF); and β-cyclodextrin. Only those members of these surfactant families which have HLB values of about 10 or greater may be used as carriers in the subject compositions.

Preferred viscosity-reducing co-solubilizers include, e.g., PHARMASOLVE™ (N-methyl-2-pyrrolidone, International Specialty Products, Wayne, N.J.); MIGLYOL™ glycerol or propylene glycol esters of caprylic and capric acids (Hütls AG, Marl, Germany); polyoxyethylated hydroxystearates (e.g., SOLUTOL™ HS 15); TWEEN™ polyoxyethylated sorbitan esters; SOFTIGEN™ polyethylene glycol esters of caprylic and capric acids (Hüls AG); modified castor oils (such as CREMOPHOR™ EL or RH 40); vegetable oils such as olive oil, polyoxyethylated fatty ethers or modified castor oils; certain saturated polyglycolyzed glycerides (such as a LABRASOL™) citrate esters such as tributyl citrate, triethyl citrate and acetyl triethyl citrate; propylene glycol, alone or in combination with PHARMASOLVE™—; ethanol; water; and lower molecular weight polyethylene glycols such as PEG 200 and 400.

The vehicle contains about 0–70% by weight of the co-solubilizer, and preferably about 10–50% by weight.

It will be noted that several of the materials identified as carriers have also been found to be effective co-solubilizers, either alone or in combination with other viscosity-reducing agents, for certain other carriers. In general, any solvent in which paclitaxel or other taxanes are at least moderately soluble at body temperature or with gentle heating can be used as a co-solubilizer in the vehicle of the novel compositions. Preferred co-solubilizers are those in which at least 25 mg/ml of paclitaxel or other taxane can be solubilized at about 20–25° C.

The concentration of the active taxane ingredient or ingredients in the composition may vary based on the solubility of the active agent in the carrier(s) or carrier(s)/co-solubilizer(s) system and on the desired total dose of taxane to be administered orally to the patient. The concentration of taxane may range from about 2 to about 500 mg/ml or mg/g of vehicle, and preferably from about 2 to about 50 mg/ml or mg/g.

The compositions of the invention may be prepared by any conventional method known to individuals of skill in the pharmaceutical arts for preparing liquid or other fluid oral formulations containing surfactant carriers and lipophilic active ingredients. Since the majority of the preferred carriers are very viscous at room temperature, and in some cases retain a relatively high viscosity even upon the addition of a minor proportion of co-solubilizer, it is generally preferred in preparing the novel compositions to mix the carriers and co-solubilizers to be used, add the taxane active ingredient, and heat the resulting mixture while stirring, for example to about 40° C. This method enables the preparation of clear solutions. Certain co-solubilizers, however, particularly PHARMASOLVE™, lower the carrier viscosity and enhance taxane solubility to such a degree that the composition can be prepared by stirring at room temperature with no heating.

It is desirable that the viscosity of the finished composition not be higher than 40,000 cps at body temperature (approximately 37° C.).

The oral compositions of the invention may be in the form of true solutions, emulsions or even suspensions, but solutions of the active taxane ingredient in the carrier or carrier/co-solubilizer system are preferred.

The present invention also comprehends methods of treating human patients afflicted with cancers, tumors, Kaposi's sarcoma, malignancies, uncontrolled tissue or cellular proliferation secondary to tissue injury, and any other disease conditions responsive to taxanes such as paclitaxel and docetaxel, and/or prodrugs and derivatives of the foregoing, with the novel orally administered pharmaceutical compositions. Among the types of carcinoma which may be treated particularly effectively with oral paclitaxel, docetaxel, other taxanes, and their prodrugs and derivatives, are hepatocellular carcinoma and liver metastases, cancers of the gastrointestinal tract, pancreas, prostate and lung, and Kaposi's sarcoma. Examples of non-cancerous disease conditions which may be effectively treated with these active agents administered orally in accordance with the present invention are uncontrolled tissue or cellular proliferation secondary to tissue injury, polycystic kidney disease, inflammatory diseases (e.g., arthritis) and malaria, including chloroquine- and pyrimethamine-resistant malaria parasites (Pouvelle et al., *J. Clin. Invest.*, 44: 413–417, 1994).

Although some of the oral pharmaceutical compositions of the invention may provide therapeutic blood levels of the taxane active ingredient when administered alone, the preferred method of the invention for treating mammalian patients (particularly human patients) suffering from taxane-responsive disease conditions is to administer the oral compositions containing the taxane target agent concomitantly with the administration of at least one dose of an oral bioavailability enhancing agent.

The preferred embodiment of the method of the invention for oral administration to humans of paclitaxel, its derivatives, analogs and prodrugs, and other taxanes comprises the oral administration of an oral absorption or bioavailability enhancing agent to a human patient simultaneously with, or prior to, or both simultaneously with and prior to the oral administration to increase the quantity of absorption of the intact target agent into the bloodstream.

The orally administered enhancing agents which may be used in practicing the preferred embodiment of the invention include, but are not limited to, the following:

Cyclosporins, including cyclosporins A through Z but particularly cyclosporin A (cyclosporine), cyclosporin F, cyclosporin D, dihydro cyclosporin A, dihydro cyclosporin C, acetyl cyclosporin A, PSC-833, SDZ-NIM 811[1] (both from Sandoz Pharmaceutical Corp). The structures of cyclosporins A–Z are described in Table 1 below.

SDZ-NIM 811 is (Me-Ile-4)-cyclosporin, an antiviral, non-immunosuppressive cyclosporin.

lesser metabolites, for example, cyclosporins B through Z, some of which exhibit substantially less immunosuppressive activity than cyclosporin A. A number of synthetic and semi-synthetic analogs have also been prepared. See generally Jergorov et al., *Phytochemistry,* 38: 403–407 (1995). The present invention comprehends natural, semi-synthetic and synthetic analogs of cyclosporins.

Cyclosporins are neutral, lipophilic, cyclic undecapeptides with molecular weights of about 1200. They are used intravenously or orally as immunosuppressants, primarily for organ transplantation and certain other conditions. Cyclosporins, particularly cyclosporine (cyclosporin A), are known inhibitors of the P-glycoprotein efflux pump and other transporter pumps as well as of certain P450 degradative enzymes, but to date no effective regimens for applying this property clinically have been developed to the point of clinical and commercial feasibility or regulatory approval.

The dosage range of the enhancing agent to be co-administered with the target agent in accordance with the invention is about 0.1 to about 20 mg/kg of patient body weight. "Co-administration" of the enhancing agent comprehends administration substantially simultaneously with the target agent (either less than 0.5 hr. before, less than 0.5 hr. after or together), from about 0.5 to about 72 hr. before

TABLE 1

Cyclosporins A–Z

| Cyclosporin | Aminoacids | | | | | | | | | | |
| --- | --- | --- | --- | --- | --- | --- | --- | --- | --- | --- | --- |
| Cy- | 1 | 2 | 3 | 4 | 5 | 6 | 7 | 8 | 9 | 10 | 11 |
| CyA | Mebmt | Abu | Sar | MeLeu | Val | MeLeu | Ala | D-Ala | MeLeu | MeLeu | MeVal |
| CyB | Mebmt | Ala | Sar | MeLeu | Val | MeLeu | Ala | D-Ala | MeLeu | MeLeu | MeVal |
| CyC | Mebmt | Thr | Sar | MeLeu | Val | MeLeu | Ala | D-Ala | MeLeu | MeLeu | MeVal |
| CyD | Mebmt | Val | Sar | MeLeu | Val | MeLeu | Ala | D-Ala | MeLeu | MeLeu | MeVal |
| CyE | Mebmt | Abu | Sar | MeLeu | Val | MeLeu | Ala | D-Ala | MeLeu | MeLeu | Val |
| CyF | Desoxy-Mebmt | Abu | Sar | MeLeu | Val | MeLeu | Ala | D-Ala | MeLeu | MeLeu | MeVal |
| CyG | Mebmt | Nva | Sar | MeLeu | Val | MeLeu | Ala | D-Ala | MeLeu | MeLeu | MeVal |
| CyH | Mebmt | Abu | Sar | MeLeu | Val | MeLeu | Ala | D-Ala | MeLeu | MeLeu | D-Mev |
| CyI | Mebmt | Val | Sar | MeLeu | Val | MeLeu | Ala | D-Ala | MeLeu | Leu | MeVal |
| CyK | Desoxy-Mebmt | Val | Sar | MeLeu | Val | MeLeu | Ala | D-Ala | MeLeu | MeLeu | MeVal |
| CyL | Bmt | Abu | Sar | MeLeu | Val | MeLeu | Ala | D-Ala | MeLeu | MeLeu | MeVal |
| CyM | Mebmt | Nva | Sar | MeLeu | Val | MeLeu | Ala | D-Ala | MeLeu | MeLeu | MeVal |
| CyN | Mebmt | Nva | Sar | MeLeu | Val | MeLeu | Ala | D-Ala | MeLeu | Leu | MeVal |
| CyO | MeLeu | Nva | Sar | MeLeu | Val | MeLeu | Ala | D-Ala | MeLeu | MeLeu | MeVal |
| CyP | Bmt | Thr | Sar | MeLeu | Val | MeLeu | Ala | D-Ala | MeLeu | MeLeu | MeVal |
| CyQ | Mebmt | Abu | Sar | Val | Val | MeLeu | Ala | D-Ala | MeLeu | MeLeu | MeVal |
| CyR | Mebmt | Abu | Sar | MeLeu | Val | Leu | Ala | D-Ala | MeLeu | Leu | MeVal |
| CyS | Mebmt | Thr | Sar | Val | Val | MeLeu | Ala | D-Ala | MeLeu | MeLeu | MeVal |
| CyT | Mebmt | Abu | Sar | MeLeu | Val | MeLeu | Ala | D-Ala | MeLeu | Leu | MeVal |
| CyU | Mebmt | Abu | Sar | MeLeu | Val | Leu | Ala | D-Ala | MeLeu | MeLeu | MeVal |
| CyV | Mebmt | Abu | Sar | MeLeu | Val | MeLeu | Ala | D-Ala | MeLeu | MeLeu | MeVal |
| CyW | Mebmt | Thr | Sar | MeLeu | Val | MeLeu | Ala | D-Ala | MeLeu | MeLeu | Val |
| CyX | Mebmt | Nva | Sar | MeLeu | Val | MeLeu | Ala | D-Ala | Leu | MeLeu | MeVal |
| CyY | Mebmt | Nva | Sar | MeLeu | Val | Leu | Ala | D-Ala | MeLeu | MeLeu | MeVal |
| CyZ | MeAminooctyl acid | Abu | Sar | MeLeu | Val | MeLeu | Ala | D-Ala | MeLeu | MeLeu | MeVal |

Cyclosporins are a group of nonpolar cyclic oligopeptides (some of which have immunosuppressant activity) produced by the genus *Tolypocladium*, including, e.g., *Tolypocladium inflatum Gams* (formerly designated as Trichoderma Polysporum), *Tolypocladium terricola* and other fungi imperfecti. The major component, cyclosporin A (cyclosporine or CsA), has been identified along with several other the administration of the target agent, or both, i.e., with one or more doses of the same or different enhancing agents given at least 0.5 hr. before and one dose given substantially simultaneously with (either together with or immediately before of after) the target agent. Additionally, "co-administration" comprehends administering more than one dose of target agent within 72 hr. after a dose of enhancing agent, in other words, the enhancing agent(s) need not be administered again before or with every administration of target agent, but may be administered intermittently during the course of treatment.

The dosage range of orally administered taxane target agents will vary from compound to compound based on its therapeutic index, the requirements of the condition being treated, the status of the subject and so forth. The method of the invention makes it possible to administer paclitaxel and other taxanes orally ranging from about 20 mg/m$^2$ to about 1000 mg/m$^2$ (based on patient body surface area) or about 0.5–30 mg/kg (based on patient body weight) as single or divided (2–3) daily doses, and maintain the plasma levels of paclitaxel in humans in the range of 50–500 ng/ml for extended periods of time (e.g., 8–12 hours) after each oral dose. These levels are at least comparable to those achieved with 96-hour IV infusion paclitaxel therapy (which causes the patient great inconvenience, discomfort, loss of quality time, infection potential, etc.). Moreover, such plasma levels of paclitaxel are more than sufficient to provide the desired pharmacological activities of the target drug, e.g., inhibition of tubulin disassembly (which occurs at levels of about 0.1 $\mu$M, or about 85 ng/ml) and inhibition of protein isoprenylation (which occurs at levels of about 0.03 $\mu$M, or about 25 ng/ml) which are directly related to its antitumor effects by inhibiting oncogene functions and other signal-transducing proteins that play a pivotal role in cell growth regulation.

Two or more different enhancing agents and/or two or more different taxane target agents may be administered together, alternately or intermittently in all of the various aspects of the method of the invention.

As indicated above, oral paclitaxel administered alone (e.g., in a solid dosage form or even in a liquid vehicle not containing an oral absorption promoting carrier) exhibits near zero bioavailability. To be considered an orally bioavailable pharmaceutical composition containing paclitaxel or other taxanes for purposes of the present invention, the composition must meet the following criterion: when the composition is administered orally to a mammalian subject (e.g., a laboratory rat or a human patient), i.e., is ingested by the subject, one hour after administration of an effective oral dose of an oral bioavailability enhancing agent, the amount of the active ingredient absorbed into the bloodstream is at least 15% of the amount absorbed when the same dose of paclitaxel is administered to the subject intravenously in a standard intravenous vehicle, for example a CREMOPHOR™ EL/ethanol vehicle. The relative percentage of absorption is determined by comparing the respective AUC (area under the curve) values of the taxane blood level vs. time curve generated upon oral administration and the corresponding curve generated upon intravenous administration.

The preferred bioavailability enhancing agent for use in making the experimental determination of whether a particular oral composition meets the 15% of IV absorption criterion is cyclsoporin A, for example a single oral dose of 5 mg/kg of CsA.

The novel pharmaceutical compositions may be administered in any known pharmaceutical dosage form. For example, the compositions may be encapsulated in a soft or hard gelatin capsule or may be administered in the form of a liquid preparation. Each dosage form may include, apart from the essential components of the composition (at least one carrier and one taxane active ingredient, and in some instances at least one co-solubilizer), conventional pharmaceutical excipients, diluents, sweeteners, flavoring agents, coloring agents and any other inert ingredients regularly included in dosage forms intended for oral administration (see, e.g., *Remington's Pharmaceutical Sciences,* 17th Ed., 1985).

Precise amounts of each of the target drugs included in the oral dosage forms will vary depending on the age, weight, disease and condition of the patient. For example, paclitaxel or other taxane dosage forms may contain sufficient quantities of the target agent to provide a daily dosage of about 20–1000 mg/m$^2$ (based on mammalian subject or patient body surface area) or about 0.5–30 mg/kg (based on mammalian subject or patient body weight) as single or divided (2–3) daily doses. Preferred dosage amounts are about 50–200 mg/m$^2$ or about 2–6 mg/kg.

Dosing schedules for the treatment method of the present invention, for example, the treatment of paclitaxel-responsive diseases with oral paclitaxel dosage forms co-administered with enhancing agents, can likewise be adjusted to account for the patient's characteristics and disease status. Preferred dosing schedules for administration of oral paclitaxel are (a) the daily administration to a patient in need thereof of 1–3 equally divided doses providing about 20–1000 mg/m$^2$ (based on body surface area), and preferably about 50–200 mg/m$^2$, with said daily administration being continued for 114 consecutive days each 2–3 weeks, or (b) administration for about one day each week. The former schedule is comparable to use of a 96-hour paclitaxel infusion every 2–3 weeks, which is considered by some a preferred IV treatment regimen.

Oral administration of taxanes in accordance with the invention may actually decrease toxic side effects in many cases as compared with currently utilized IV therapy. Rather than producing a sudden and rapid high concentration in blood levels as is usually the case with an IV infusion, absorption of the active agent through the gut wall (promoted by the enhancing agents), provides a more gradual appearance in the blood levels and a stable, steady-state maintenance of those levels at or close to the ideal range for a long period of time.

In a further embodiment of the present invention, the oral compositions of the invention may be administered in a two-part medicament system. Thus, for example, there may be certain carriers coming within the scope of the invention which are desirable for use in vehicles for certain taxane agents because of their ability to solubilize the taxane and promote its oral absorption, but the carrier may be chemically or physically incompatible with desired adjunctive ingredients such as flavoring or coloring agents. In such cases, the active ingredient can be administered to the patient as the first part of the medicament in a relatively small volume of any suitable liquid solubilizing vehicle (such as water, CREMOPHOR™ or ethanol), which may be sweetened, flavored or colored as desired to mask the unpleasant taste of the vehicle and render it more palatable. The administration of the active ingredient can be followed by administration of the second part of the medicament: a larger volume of fluid, for example 1 to 8 fluid ounces (30–240 ml), containing at least one carrier or a carrier/co-solubilizer system in accordance with the invention. It has been discovered that administration of the second, "chaser" formulation a short time after the taxane active ingredient can retard precipitation of the taxane which might otherwise occur upon entry into the gastric fluid and promote oral absorption to a degree comparable to that observed when the taxane is intermixed with the carrier and administered simultaneously.

Illustrative examples of "chaser" formulations which may be used in a two-part oral taxane medicament include:

a) 2–20% (by weight) Vitamin E TPGS+water q.s.;
b) 2–25% Vitamin E TPGS+2–25% PHARMASOLVE™+water q.s.;
c) 2–20% Vitamin E TPGS+2–25% propylene glycol+water q.s.

Pursuant to yet another aspect of the invention, the oral compositions of the invention can contain not only one or more taxane active ingredients but also one or more bioavailability enhancing agents in a combination dosage form. For example, such combination dosage form may contain from about 0.1 to about 20 mg/kg (based on average patient body weight) of one or more of cyclosporins A, D, C, F and G, dihydro CsA, dihydro CsC and acetyl CsA together with about 20 to about 1000 mg/m² (based on average patient body surface area), and preferably about 50–200 mg/m², of paclitaxel, docetaxel, other taxanes or paclitaxel or docetaxel derivatives.

The compositions and methods of the present invention provide many advantages in comparison with prior art intravenous compositions containing paclitaxel and other taxanes and prior art intravenous administration regimens. Apart from the issues of decreased toxicity, patient convenience and comfort, ease of administration and lowered expense, discussed previously, the invention makes it possible to administer powerful taxane antitumor agents to patients with greatly reduced likelihood of allergic hypersensitivity reactions which are common with IV administration. Thus, the need for pre-medication regimens of H-1 and H-2 blockers plus steroids can be eliminated.

The present invention also makes it possible to give taxanes, e.g., paclitaxel, in comparatively infrequent daily doses (e.g., about twice/day) and according to schedules that would otherwise not be possible or practical with the intravenous route. The use of the bioavailability enhancer (e.g., cyclosporin A) promotes oral absorption of paclitaxel for the first dose and if a second paclitaxel dose is to be given later in the day, the use of additional cyclosporin A may not even be needed. Thus, paclitaxel could be given intermittently as single dose on a fixed schedule (weekly, biweekly, etc.) or chronically, over a period of consecutive days (e.g., 4 days) every 24 weeks with the goal of keeping the levels within a safe and effective "window".

The following examples illustrate various aspects of the invention. These examples are not intended, however, to limit the invention in any way or to set forth specific active ingredients, carriers, co-solubilizers, enhancing agents, dosage ranges, testing procedures or other parameters which must be used exclusively to practice the invention.

EXAMPLE 1

Animal Screening Model

Groups of three male rats each were fasted for 16–18 hours prior to dosing with ³H-radiolabeled paclitaxel. Each group of animals received one oral dose of cyclosporin A (5 mg/kg) prior to dosing with experimental oral paclitaxel formulation. One hour subsequent to cyclosporin dosing, each group received approximately 9 mg/kg of paclitaxel orally in the form of a composition according to the invention. Each group received a different oral formulation.

Blood samples were collected from each animal at 0.5, 1, 2, 3, 4, 6, 8, 12 and 24 hours post-dose of paclitaxel. The blood samples were combusted and assayed for total radioactivity.

The total blood radioactivity levels (corresponding to concentration in the blood of ³H-paclitaxel) were plotted on a graph vs. time post-dose. Data for each group of rats were compiled in the form of mean AUC, $C_{max}$ and $T_{max}$.

The percentage of absorption of ³H-paclitaxel for each group of animals was calculated by comparing the mean AUC value for the group to the corresponding mean AUC of a reference group of rats administered ³H-paclitaxel (9 mg/kg) intravenously in the form of PAXENE™ (Baker Norton Pharmaceuticals, Miami Fla.) which includes CREMOPHOR™ EL, ethanol and citric acid.

Table 2 lists all carriers and carrier/co-solubilizer combinations which were formulated into oral compositions containing paclitaxel in accordance with the invention, were tested in rats in accordance with the foregoing procedure and were found to yield percentage absorption values in the experimental animals of 15% or greater in comparison with IV paclitaxel.

TABLE 2

Carriers and carrier/co-solubilizer combinations which achieved greater than 15% paclitaxel absorption

| Carriers | | | | Co-solubilizers | | | |
|---|---|---|---|---|---|---|---|
| TPGS | Pharmasolve | Propylene glycol | Mygliols | Softigen | PEG 200 & 400 | Propylene glycol/ Pharmasolve | PEG 200 & 400/Pharmasolve |
| Gelucire 44/14 | Pharmasolve | Mygliols | Olive oil/ Brij 97 | Olive oil/ Cremophor RH 40 | Olive oil/TPGS | Cremophor EL | Cremophor RH 40 |
| Gelucire 44/14 | Labrasol | TPGS/ Solutol HS 15 | Tween 80 | PEG 400 | | | |
| Gelucire 50/13 | Tween 80 | PEG 400 | Cremophor EL | | | | |
| Cremophor EL | Pharmasolve | Citrate esters | Ethanol/water | Ethanol | | | |
| Cremophor RH 40 | Ethanol/water | | | | | | |
| Myrj 49 | Pharmasolve | | | | | | |
| Myrj 52 | Pharmasolve | Propylene glycol | | | | | |
| Myrj 53 | Pharmasolve | | | | | | |
| Tween 40* | | | | | | | |
| Tween 60* | | | | | | | |
| Tween 80* | Ethanol | Citrate esters | Olive oil | PEG 400 | Water | | |
| Crillet 6* | | | | | | | |
| Emsorb 2726 | Pharmasolve | | | | | | |
| Solutol HS 15* | | | | | | | |
| Brij 76 | Pharmasolve | | | | | | |
| Brij 78 | Pharmasolve | | | | | | |

TABLE 2-continued

Carriers and carrier/co-solubilizer combinations which achieved greater than 15% paclitaxel absorption

| Carriers | Co-solubilizers |
|---|---|
| Brij 98 | Pharmasolve |
| Crovol A-40* | |
| Crovol M-40* | |
| β-Cyclodextrin | Water |

*Have been demonstrated to work as both solubilizer and carrier
Note: All carriers listed above can solubilize paclitaxel greater than 25 mg/ml at 37° C.

EXAMPLE 2

Polyoxyethylated (POE) Sorbitan Fatty Acid Esters as Carriers

Table 3 lists vehicle formulations including certain POE sorbitan fatty acid esters as carriers for oral paclitaxel, alone or in combination with a co-solubilizer. In formulations where more than one component is present in the vehicle, the respective weight ratios of the components is given. Each of these formulations was tested in the animal model described in Example 1 and found to yield a percentage absorption of paclitaxel upon oral administration greater (in some cases far greater) than 15% of a roughly comparable dose of paclitaxel administered intravenously. The table sets forth the total dose of paclitaxel incorporated into each vehicle as actually administered to the experimental animals, the concentration of paclitaxel in the composition, the HLB value of the carrier, the mean AUC value for the group of rats receiving the formulation and the percentage of paclitaxel absorption in comparison with rats receiving IV administration.

TABLE 3

Absorption Results of Polyoxyethylated (POE) Sorbitan Fatty Acid Esters Surfactants as Carriers

| FORMULATIONS | Dose [mg/kg] | Conc. [mg/ml] | HLB | AUC μg.eqxhr/ml | % ABS* |
|---|---|---|---|---|---|
| POE 20 sorbitan monolaurate (Tween 20) | 10.2 | 18 | 16.7 | 17.2 | 54.6 |
| POE 20 sorbitan monopalmitate (Tween 40) | 10.2 | 18 | 15.6 | 17.6 | 55.9 |
| POE 20 sorbitan monostearate (Tween 60) | 8.9 | 25 | 14.9 | 17.1 | 62.3 |
| POE 20 sorbitan tristearate (Tween 65) | 9.4 | 25 | 10.5 | 6.15 | 21.1 |
| POE 20 sorbitan monooleate (Tween 80) | 9.0 | 18 | 15.0 | 11.4 | 40.9 |
| POE 20 sorbitan monoisostearate (Crillet 6) | 9.3 | 20 | 14.9 | 13.6 | 47.5 |
| POE 40 sorbitan diisostearate/Pharmasolve (3:1) [Emsorb 2726] | 10.2 | 25 | 15.0* | 7.76 | 24.6 |

*Percent absorption versus paclitaxel IV AUC (same for Tables 4–11)

EXAMPLE 3

POE Alkyl Ethers as Carriers

Table 4 pertains to vehicle formulations containing POE alkyl ethers as carriers. The data set forth correspond to the data described in the preceding example with respect to Table 3.

TABLE 4

Absorption Results of Polyoxyethylated (POE) Alkyl Ethers Surfactants as Carriers

| FORMULATIONS | Dose [mg/kg] | Conc. [mg/ml] | HLB | AUC μg.eqxhr/ml | % ABS |
|---|---|---|---|---|---|
| POE 10 stearyl ether/ Pharmasolve (3:1) [Brij 76] | 10.2 | 18 | 12.4* | 9.54 | 30.3 |
| POE 20 stearyl ether/ Pharmasolve (3:1) [Brij 78] | 9.5 | 18 | 15.3* | 11.4 | 38.7 |
| POE 20 oleyl ether/ Pharmasolve (3:1) [Brij 98] | 9.6 | 25 | 15.3* | 5.89 | 20.9 |

EXAMPLE 4

POE Stearates as Carriers

Table 5 pertains to vehicle formulations containing POE stearates as carriers. The data set forth correspond to the data described in Example 2 with respect to Table 3.

TABLE 5

Absorption Results of Polyoxyethylated (POE) Stearates as Carriers

| FORMULATIONS | Dose [mg/kg] | Conc. [mg/ml] | HLB | AUC μg.eqxhr/ml | % ABS |
|---|---|---|---|---|---|
| POE 20 stearate ester/ Pharmasolve (3:1) [Myrj 49] | 9.2 | 25 | 15.0* | 10.3 | 36.4 |
| POE 40 stearate ester/ Pharmasolve (3:1) [Myrj 52] | 9.4 | 18 | 16.9* | 16.2 | 57.3 |
| POE 50 stearate ester/ Pharmasolve (3:1) [Myrj 53] | 10.0 | 25 | 17.9* | 7.01 | 22.3 |

EXAMPLE 5

Ethoxylated Modified Triglycerides as Carriers

Table 6 pertains to vehicle formulations containing ethoxylated modified triglycerides as carriers. The data set forth correspond to the data described in Example 2 with respect to Table 3.

TABLE 6

Absorption Results of Ethoxylated Modified Triglycerides as Carriers

| FORMULATIONS | Dose [mg/kg] | Conc. [mg/ml] | HLB | AUC μg.eqxhr/ml | % ABS |
|---|---|---|---|---|---|
| PEG-20 Almond Glycerides (Crovol A-40) | 9.5 | 20 | 10 | 8.06 | 27.6 |
| PEG-20 Corn Glycerides (Crovol M-40) | 9.6 | 20 | 10 | 7.46 | 25.3 |

EXAMPLE 6

POE 660 Hydroxystearates as Carriers

Table 7 pertains to vehicle formulations containing POE 660 hydroxystearates as carriers. The data set forth correspond to the data described in Example 2 with respect to Table 3.

TABLE 7

Absorption Results of Polyoxyethylated (POE) 660 Hydroxystearate as Carrier

| FORMULATIONS | Dose [mg/kg] | Conc. [mg/ml] | HLB | AUC μg.eqxhr/ml | % ABS |
|---|---|---|---|---|---|
| POE 660 hydroxystearate (Solutol HS 15) | 9.1 | 25 | ~14 | 10.8 | 38.4 |
| Gelucire 44/14 + Solutol HS + TPGS (2:1:1) | 9.3 | 25 | ~14 | 6.54 | 22.8 |

EXAMPLE 7

Saturated Polyglycolized Glycerides as Carriers

Table 8 pertains to vehicle formulations containing saturated polyglycolyzed glycerides as carriers. The data set forth correspond to the data described in Example 2 with respect to Table 3.

TABLE 8

Absorption Results of Saturated Polyglycolized Glycerides as Carriers

| FORMULATIONS | Dose [mg/kg] | Conc. [mg/ml] | AUC μg.eqxhr/ml | % ABS |
|---|---|---|---|---|
| Gelucire 44/14 + PEG 400 (6:1) | 10.3 | 25 | 11.9 | 37.4 |
| Gelucire 44/14 + Labrasol (6:1) | 9.3 | 25 | 12.1 | 42.1 |
| Gelucire 44/14 + Mygliol 810 (6:1) | 8.7 | 25 | 4.75 | 17.6 |
| Gelucire 44/14 + Mygliol 818 (6:1) | 10.3 | 25 | 8.45 | 26.6 |
| Gelucire 44/14 + Mygliol 840 (6:1) | 9.5 | 25 | 6.48 | 22.0 |
| Gelucire 44/14 + Cremophore RH 40 (6:1) | 9.5 | 25 | 10.7 | 36.6 |
| Gelucire 44/14 + Cremophor EL (6:1) | 9.8 | 25 | 11.5 | 38.1 |
| Gelucire 44/14 + Solutol HS + TPGS (2:1:1) | 9.3 | 25 | 6.54 | 22.8 |
| Gelucire 44/14 + Olive Oil + Tween 80 (2:1:1) | 9.6 | 20 | 11.9 | 39.9 |
| Gelucire 44/14 + Olive Oil + TPGS (2:1:1) | 9.6 | 20 | 9.83 | 33.2 |
| Gelucire 44/14 + Olive Oil + POE 10 Oleyl (2:1:1) | 9.6 | 20 | 9.07 | 30.6 |
| Gelucire 44/14 + Olive Oil + Cremophor RH 40 (2:1:1) | 9.1 | 20 | 7.73 | 27.5 |
| Gelucire 44/14 + Tween 80 (6:1) | 9.7 | 25 | 10.05 | 33.5 |
| Gelucire 50/13 + Tween 80 (5:2) | 9.4 | 25 | 8.21 | 28.4 |
| Gelucire 50/13 + PEG 400 (6:1) | 9.3 | 25 | 6.46 | 22.5 |
| Gelucire 50/13 + Cremophor EL (6:1) | 9.1 | 25 | 8.11 | 28.9 |

Labrasol: Saturated polyglycolyzed C8–C10 glycerides (HLB=14)
Mygliols: Neutral oils (saturated coconut and palmkernel fatty acids) mainly C8–C10 fatty acids
Cremophor EL: Polyoxyl 35 castor oil (HLB 12–14)
Cremophor RH 40: Polyoxyl 40 Hydrogenated castor oil (HLB 14–16)

EXAMPLE 8

Vitamin E TPGS Systems as Carriers

Table 9 pertains to vehicle formulations containing Vitamin E TPGS systems as carriers. The data set forth correspond to the data described in Example 2 with respect to Table 3.

TABLE 9

Absorption Results of TPGS Systems as Carriers

| FORMULATIONS | Dose [mg/kg] | Conc. [mg/ml] | AUC $\mu$g.eqxhr/ml | % ABS* |
|---|---|---|---|---|
| TPGS + Pharmasolve (1.5:1) | 8.2 | 25 | 8.93 | 35.2 |
| TPGS + Pharmasolve (1:1) | 9.5 | 25 | 8.72 | 29.8 |
| TPGS + Pharmasolve (2:1) | 9.1 | 25 | 8.83 | 31.4 |
| TPGS + Propylene glycol (1:1) | 8.5 | 20 | 9.65 | 36.9 |
| TPGS + Pharmasolve + PEG 200 (2:1:1) | 9.0 | 25 | 8.31 | 29.8 |
| TPGS + Pharmasolve + PEG 400 (2:1:1) | 8.2 | 25 | 6.62 | 26.3 |
| TPGS + Pharmasolve + PG (2:1:1) | 8.9 | 25 | 8.07 | 29.3 |
| TPGS + Mygliol 810 (1:1) | 9.1 | 25 | 5.65 | 20.0 |
| TPGS + Softigen 767 (1:1) | 10.2 | 25 | 8.66 | 27.5 |
| TPGS + PEG 200 (1:1) | 8.3 | 25 | 7.75 | 30.4 |
| TPGS + PEG 400 (1:1) | 9.6 | 25 | 7.32 | 24.6 |

Softigen 767: PEG-6-Caprylic/Capric Glycerides

EXAMPLE 9

POE and Hydrogenated Castor Oil Derivatives as Carriers

Table 10 pertains to vehicle formulations containing POE and hydrogenated castor oil derivatives as carriers. The data set forth correspond to the data described in Example 2 with respect to Table 3.

TABLE 10

Absorption Results of Polyoxyethylated Castor Oil (Cremophor) Derivatives Systems as Carriers

| FORMULATIONS | Dose [mg/kg] | Conc. [mg/ml] | AUC $\mu$g.eqxhr/ml | % ABS |
|---|---|---|---|---|
| IV Paxene | 10.0 | 6 | 11.15 | 37.2 |
| Cremophor EL + Ethanol + Water (1:1:8) | 9.2 | 1.3 | 6.07 | 21.5 |
| IV Paxene + Water (1:1) | 8.9 | 3 | 8.70 | 31.8 |
| IV Paxene + Water (1:5) | 9.1 | 1 | 10.76 | 38.5 |
| Cremophor EL + Pharmasolve (1:1) | 8.6 | 20 | 6.74 | 25.3 |
| Cremophor EL + TBC (1:1) | 9.0 | 20 | 9.35 | 31.9 |
| Cremophor EL + Gelucire 44/14 (1:6) | 9.8 | 25 | 11.5 | 38.1 |
| Cremophor EL + Gelucire 50/13 (1:6) | 9.1 | 25 | 8.11 | 28.9 |
| Cremophor RH 40 + Ethanol + Water (1:1:2) | 9.0 | 3 | 7.14 | 25.7 |
| Cremophor RH 40 + Gelucire 44/14 (1:6) | 9.5 | 25 | 10.7 | 36.6 |
| Cremophor RH 40 + Gelucire 44/14 + Olive Oil (1:2:1) | 9.1 | 20 | 7.73 | 27.5 |

EXAMPLE 10

Polysorbate 80 Carriers

Table 11 pertains to vehicle formulations containing polysorbate 80 as at least one of the carriers. The data set forth correspond to the data described in Example 2 with respect to Table 3.

TABLE 11

Absorption Results of Polysorbate 80 (Tween 80) Systems as Carrierts

| FORMULATIONS | Dose [mg/kg] | Conc. [mg/ml] | AUC µg.eqxhr/ml | % ABS |
|---|---|---|---|---|
| Polysorbate 80 | 9.0 | 18 | 11.4 | 40.9 |
| Polysorbate 80 + Ethanol + Water (1:1:8) | 8.0 | 1.2 | 7.92 | 31.2 |
| Polysorbate 80 + Ethanol (3:1) | 8.9 | 18 | 9.97 | 36.3 |
| Polysorbate 80 + Water (3:1) | 8.2 | 18 | 7.15 | 28.3 |
| Polysorbate 80 + TBC (1:1) | 9.5 | 20 | 9.12 | 31.2 |
| Polysorbate 80 + ATEC (1:1) | 9.1 | 20 | 8.50 | 30.3 |
| Polysorbate 80 + Olive oil (3:1) | 9.0 | 20 | 13.3 | 43.7 |
| Polysorbate 80 + PEG 400 (1:1) | 9.7 | 20 | 9.41 | 31.5 |
| Polysorbate 80 + Gelucire 44/14 + Olive Oil (1:2:1) | 9.6 | 20 | 11.9 | 39.9 |
| Polysorbate 80 + Gelucire 44/14 (1:6) | 9.7 | 25 | 10.05 | 33.5 |

TBC = Tributyl citrate (citrate ester)
ATEC = Acetyl triethyl citrate (citrate ester)

It has thus been shown that there are provided compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

We claim:

1. A pharmaceutical composition for oral administration to a mammalian subject, comprising:
   a) a taxane or taxane derivative as active ingredient; and
   b) a vehicle comprising i) at least about 30% by weight of a carrier comprising Vitamin E TPGS; and ii) a co-solubilizer comprising ethanol and propylene glycol, or ethanol and a lower molecular weight polyethylene glycol (PEG).

2. The composition of claim 1, wherein said co-solubilizer comprises ethanol and propylene glycol.

3. The composition of claim 1, wherein said vehicle comprises about 30–90% by weight of Vitamin E TPGS.

4. The composition of claim 1, wherein said taxane is dissolved or dispersed in said vehicle.

5. The composition of claim 1, wherein said taxane in present in said vehicle in a concentration of about 2–500 mg/ml or mg/g.

6. The composition of claim 5, wherein the concentration of said taxane in said vehicle is about 2–50 mg/ml or mg/g.

7. The composition of claim 1, wherein said vehicle comprises about 0 to 70% by weight of said co-solubilizer.

8. The composition of claim 1, wherein said vehicle comprises about 10–50% by weight of said co-solubilizer.

9. The composition of claim 1, wherein said co-solubilizer comprises ethanol and said lower molecular weight PEG.

10. The composition of claim 9, wherein said lower molecular weight PEG comprises PEG 200 or PEG 400.

11. The composition of claim 10, wherein said lower molecular weight PEG comprises PEG 400.

12. The composition of claim 1, wherein said taxane is docetaxel.

13. The composition of claim 1, wherein said taxane is paclitaxel.

14. The composition of claim 13, wherein said co-solubilizer comprises ethanol and propylene glycol.

15. The composition of claim 14, wherein said co-solubilizer is present in an amount of 50% to 70% by weight of said vehicle.

16. The composition of claim 13, which is in a liquid oral dosage form.

17. The composition of claim 13, wherein said co-solubilizer comprises ethanol and a lower molecular weight polyethylene glycol (PEG).

18. The composition of claim 17, wherein said co-solubilizer is present in an amount of about 10–50% by weight of said vehicle.

19. The composition of claim 17, wherein said lower molecular weight PEG is PEG 400.

20. The composition of claim 17, which is in an oral dosage form of a soft or hard gelatin capsule.

21. The composition of claim 1, further comprising a pharmaceutical excipient, diluent, sweetener, flavoring agent or coloring agent.

22. The composition of claim 1, further comprising a sweetener, flavoring agent or coloring agent.

23. The composition of claim 1, which is in an oral dosage form that contains about 20–1,000 mg/m$^2$ of said taxane based on the body surface of the mammalian subject.

24. The composition of claim 1, which is in an oral dosage form that contains about 50–200 mg/m$^2$ of said taxane based on the body surface of the mammalian subject.

25. The composition of claim 1, which is in an oral dosage form that contains about 0.5–30 mg/kg of said taxane based on the weight of the mammalian subject.

26. The composition of claim 1, which is in an oral dosage form that contains about 2–6 mg/kg of said taxane based on the weight of the mammalian subject.

27. A pharmaceutical composition for oral administration to a mammalian subject, comprising:
   a taxane or taxane derivative as active ingredient;
   a vehicle comprising i) at least about 30% by weight of a carrier comprising Vitamin E TPGS, and ii) a co-solubilizer comprising ethanol in an amount of about 10–50% by weight of said vehicle; wherein said composition is in an oral dosage form of a hard or soft gelatin capsule.

28. The composition of claim 27, wherein said taxane is docetaxel.

29. The composition of claim 27, wherein said taxane is paclitaxel.

30. A pharmaceutical composition for oral administration to a mammalian subject, comprising:
   a taxane or taxane derivative as active ingredient;
   a vehicle comprising i) at least about 30% by weight of a carrier comprising Vitamin E TPGS, and ii) a co-solubilizer comprising propylene glycol.

31. The composition of claim 30, wherein said carrier is present in an amount of about 30–90% by weight of said vehicle.

32. The composition of claim 30, wherein propylene glycol is present in an amount of about 0 to 70% by weight of said vehicle.

33. The composition of claim 31, wherein propylene glycol is present in an amount of about 10–50% by weight of said vehicle.

34. The composition of claim 33, wherein said co-solubilizer further comprises ethanol.

35. The composition of claim 34, wherein said co-solubilizer is present in an amount of 50–70% by weight of said vehicle.

36. The composition of claim 34, which is a solution or a suspension.

37. The composition of claim 35, which is an oral dosage form of a liquid.

38. The composition of claim 30, wherein said taxane is docetaxel.

39. The composition of claim 30, wherein said taxane is paclitaxel.

40. The composition of claim 34, wherein said taxane is paclitaxel.

41. The composition of claim 35, wherein said taxane is paclitaxel.

42. The composition of claim 36, wherein said taxane is paclitaxel.

43. A pharmaceutical composition for oral administration to a mammalian subject, comprising:
   a) a taxane or taxane derivative as active ingredient;
   b) a vehicle comprising i) at least 30% by weight of a carrier comprising Vitamin E TPGS, and ii) a co-solubilizer comprising a lower molecular weight PEG selected from the group consisting of PEG 200 and PEG 400, wherein said co-solubilizer is present in an amount of about 10–50% by weight of said vehicle.

44. The composition of claim 43, wherein said composition is a solution or a suspension.

45. The composition of claim 43, wherein said co-solubilizer further comprises ethanol.

46. The composition of claim 45, wherein said lower molecular weight PEG is PEG 400.

47. The composition of claim 43, which is in an oral dosage form of a soft or hard gelatin capsule.

48. The composition of claim 43, wherein said taxane is docetaxel.

49. The composition of claim 43, wherein said taxane is paclitaxel.

50. The composition of claim 45, wherein said taxane is paclitaxel.

51. The composition of claim 46, wherein said taxane is paclitaxel.

52. A pharmaceutical composition for oral administration to a mammalian subject, comprising:
   a taxane or taxane derivative as active ingredient;
   a vehicle comprising i) at least about 30% by weight of a carrier comprising Vitamin E TPGS, and ii) a co-solubilizer comprising N-methyl-2-pyrrolidone, glycerol or propylene glycol esters of caprylic and capric acids, polyethylene glycol esters of caprylic and capric acids, saturated coconut and palmkernel fatty acids, or saturated polyglycolized glycerides.

53. The composition of claim 52, wherein said co-solubilizer comprises N-methyl-2-pyrrolidone.

54. The composition of claim 52, wherein said co-solubilizer comprises glycerol or propylene glycol esters of caprylic and capric acids.

55. The composition of claim 54, wherein said glycerol or propylene glycol esters of caprylic and capric acids comprise PEG-6-caprylic/capric glycerides.

56. The composition of claim 52, wherein said co-solubilizer comprises polyethylene glycol esters of caprylic and capric acids.

57. The composition of claim 52, wherein said co-solubilizer comprises saturated coconut and palm kernel fatty acids.

58. The composition of claim 57, wherein said saturated coconut and palm kernel fatty acids comprise saturated coconut and palm kernel $C_8$–$C_{10}$ fatty acids.

59. The composition of claim 52, wherein said co-solubilizer comprises saturated polyglycolized glycerides.

60. The composition of claim 59, wherein said saturated polyglycolized glycerides comprise glycerides of C8–C18 fatty acids.

61. The composition of claim 52, wherein said co-solubilizer further comprises ethanol.

62. The composition of claim 52, wherein said co-solubilizer is present in an amount of about 10–500% by weight of said vehicle.

63. The composition of claim 52, wherein said taxane is docetaxel.

64. The composition of claim 52, wherein said taxane is paclitaxel.

65. The composition of claim 60, wherein said taxane is paclitaxel.

66. The composition of claim 61, wherein said taxane is paclitaxel.

67. A method of treating a mammalian subject suffering from a taxane-responsive disease condition, comprising the oral administration to the subject of a pharmaceutical composition, comprising:
   a) a taxane or taxane derivative as active ingredient; and
   b) a vehicle comprising i) at least about 30% by weight of a carrier comprising Vitamin E TPGS; and ii) a co-solubilizer comprising ethanol and propylene glycol, or ethanol and a lower molecular weight polyethylene glycol (PEG).

68. The method of claim 67, wherein the co-solubilizer comprises ethanol and propylene glycol.

69. The method of claim 67, wherein the vehicle comprises about 30–90% by weight of Vitamin E TPGS.

70. The method of claim 67, wherein the taxane is dissolved or dispersed in the vehicle.

71. The method of claim 67, wherein the concentration of the taxane in the vehicle is about 2–500 mg/ml or mg/g.

72. The method of claim 71, wherein the concentration of the taxane in the vehicle is about 2–50 mg/ml or mg/g.

73. The method of claim 67, wherein the vehicle comprises about 0 to 70% by weight of the co-solubilizer.

74. The method of claim 67, wherein the vehicle comprises about 10–50% by weight of the co-solubilizer.

75. The method of claim 67, wherein the co-solubilizer comprises ethanol and the lower molecular weight PEG.

76. The method of claim 75, wherein the lower molecular weight PEG comprises PEG 200 or PEG 400.

77. The method of claim 76, wherein the lower molecular weight PEG comprises PEG 400.

78. The method of claim 67, wherein the taxane is docetaxel.

79. The method of claim 67, wherein the taxane is paclitaxel.

80. The method of claim 79, wherein the co-solubilizer comprises ethanol and propylene glycol.

81. The method of claim 80, wherein the co-solubilizer is present in an amount of 50% to 70% by weight of the vehicle.

82. The method of claim 79, wherein the composition is in a liquid oral dosage form.

83. The method of claim 79, wherein the co-solubilizer comprises ethanol and a lower molecular weight polyethylene glycol (PEG).

84. The method of claim 83, wherein the co-solubilizer is present in an amount of about 10–50% by weight of the vehicle.

85. The method of claim 83, wherein the lower molecular weight PEG is PEG 400.

86. The method of claim 83, wherein the composition is in an oral dosage form of a soft or hard gelatin capsule.

87. The method of claim 67, wherein the composition further comprises a pharmaceutical excipient, diluent, sweetener, flavoring agent or coloring agent.

88. The method of claim 67, wherein the composition further comprises a sweetener, flavoring agent or coloring agent.

89. The method of claim 67, wherein the composition is in an oral dosage form that contains about 20–1,000 mg/m² of the taxane based on the body surface of the mammalian subject.

90. The method of claim 67, wherein the composition is in an oral dosage form that contains about 50–200 mg/m² of the taxane based on the body surface of the mammalian subject.

91. The method of claim 67, wherein the composition is in an oral dosage form that contains about 0.5–30 mg/kg of the taxane based on the weight of the mammalian subject.

92. The method of claim 67, wherein the composition is in an oral dosage form that contains about 2–6 mg/kg of the taxane based on the weight of the mammalian subject.

93. A method of treating a mammalian subject suffering from a taxane-responsive disease condition, comprising the oral administration to the subject of a pharmaceutical composition, comprising:
 a taxane or taxane derivative as active ingredient;
 a vehicle comprising i) at least about 30% by weight of a carrier comprising Vitamin E TPGS, and ii) a co-solubilizer comprising ethanol in an amount of about 10–50% by weight of said vehicle.

94. The method of claim 93, wherein the taxane is docetaxel.

95. The method of claim 93, wherein the taxane is paclitaxel.

96. A method of treating a mammalian subject suffering from a taxane-responsive disease condition, comprising the oral administration to the subject of a pharmaceutical composition, comprising:
 a taxane or taxane derivative as active ingredient;
 a vehicle comprising i) at least about 30% by weight of a carrier comprising Vitamin E TPGS, and ii) a co-solubilizer comprising propylene glycol.

97. The method of claim 96, wherein the carrier is present in an amount of about 30–90% by weight of the vehicle.

98. The method of claim 96, wherein the propylene glycol is present in an amount of about 0 to 70% by weight of the vehicle.

99. The method of claim 97, wherein the propylene glycol is present in an amount of about 10–50% by weight of the vehicle.

100. The method of claim 99, wherein the co-solubilizer further comprises ethanol.

101. The method of claim 100, wherein the co-solubilizer is present in an amount of 50–70% by weight of the vehicle.

102. The method of claim 100, wherein the composition is a solution or a suspension.

103. The method of claim 101, wherein the composition is in an oral dosage form of a liquid.

104. The method of claim 96, wherein the taxane is docetaxel.

105. The method of claim 96, wherein the taxane is paclitaxel.

106. The method of claim 100, wherein the taxane is paclitaxel.

107. The method of claim 101, wherein the taxane is paclitaxel.

108. The method of claim 102, wherein the taxane is paclitaxel.

109. A method of treating a mammalian subject suffering from a taxane-responsive disease condition, comprising the oral administration to the subject of a pharmaceutical composition, comprising:
 a) a taxane or taxane derivative as active ingredient;
 b) a vehicle comprising i) at least 30% by weight of a carrier comprising Vitamin E TPGS, and ii) a co-solubilizer comprising a lower molecular weight PEG selected from the group consisting of PEG 200 and PEG 400, wherein said co-solubilizer is present in an amount of about 10–50% by weight of the vehicle.

110. The method of claim 109, wherein the composition is a solution or a suspension.

111. The method of claim 109, wherein the co-solubilizer further comprises ethanol.

112. The method of claim 111, wherein the lower molecular weight PEG is PEG 400.

113. The method of claim 109, wherein the composition is in an oral dosage form of a soft or hard gelatin capsule.

114. The method of claim 109, wherein the taxane is docetaxel.

115. The method of claim 109, wherein the taxane is paclitaxel.

116. The method of claim 111, wherein the taxane is paclitaxel.

117. The method of claim 112, wherein the taxane is paclitaxel.

118. A method of treating a mammalian subject suffering from a taxane-responsive disease condition, comprising the oral administration to the subject of a pharmaceutical composition, comprising:
 a taxane or taxane derivative as active ingredient;
 a vehicle comprising i) at least about 30% by weight of a carrier comprising Vitamin E TPGS, and ii) a co-solubilizer comprising N-methyl-2-pyrrolidone, glycerol or propylene glycol esters of caprylic and capric acids, polyethylene glycol esters of caprylic and capric acids, saturated coconut and palm kernel fatty acids, or saturated polyglycolized glycerides.

119. The method of claim 118, wherein the co-solubilizer comprises N-methyl-2-pyrrolidone.

120. The method of claim 118, wherein the co-solubilizer comprises glycerol or propylene glycol esters of caprylic and capric acids.

121. The method of claim 120, wherein the glycerol or propylene glycol esters of caprylic and capric acids comprise PEG-6-caprylic/capric glycerides.

122. The method of claim 118, wherein the co-solubilizer comprises polyethylene glycol esters of caprylic and capric acids.

123. The method of claim 118, wherein the co-solubilizer comprises saturated coconut and palm kernel fatty acids.

124. The method of claim 123, wherein the saturated coconut and palm kernel fatty acids comprise saturated coconut and palmkernel $C_8$–$C_{10}$ fatty acids.

125. The method of claim 118, wherein the co-solubilizer comprises saturated polyglycolized glycerides.

126. The method of claim 125, wherein the saturated polyglycolized glycerides comprise glycerides of $C_8$–$C_{18}$ fatty acids.

127. The method of claim 118, wherein the co-solubilizer further comprises ethanol.

128. The method of claim 118, wherein the co-solubilizer is present in an amount of about 10–50% by weight of said vehicle.

129. The method of claim 118, wherein the taxane is docetaxel.

130. The method of claim 118, wherein the taxane is paclitaxel.

131. The method of claim 126, wherein the taxane is paclitaxel.

132. The method of claim 127, wherein the taxane is paclitaxel.

133. The method of any one of claims 67, 93, 96, 106, 109 and 118, further comprising the oral co-administration to the subject of an effective bioavailability-enhancing amount of an oral bioavailability enhancing agent.

134. The method of claim 133, wherein the effective amount of the enhancing agent is about 0.1–20 mg/kg based on the weight of the mammalian subject.

135. The method of claim 133, wherein the enhancing agent is administered either:
 a) about 0.5–72 hours before;
 b) less than 0.5 hours before, together with or less than 0.5 hours after, or
 c) both about 0.5–72 hours before and again less than 0.5 hours before, together with or less than 0.5 hours after administration of the composition comprising the taxane.

136. The method of claim 135, wherein said enhancing agent is administered one hour before the administration of the composition.

137. The method of claim 133, wherein the enhancing agent is a cyclosporin.

138. The method of claim 137, wherein the cyclosporin is cyclosporin A.

139. The method of claim 137, wherein the cyclosporin is selected from the group consisting of cyclosporins A–Z, (Me-Ile-4)-cyclosporin, dihydro cyclosporin A, dihydro cyclosporin C, and acetyl cyclosporin A.

140. The method of claim 137, wherein said cyclosporin is selected from the group consisting of cyclosporin A, cyclosporin C, cyclosporin D, cyclosporin F, dihydro cyclosporin A, dihydro cyclosporin C, and acetyl cyclosporin A.

141. The method of claim 133, wherein the disease condition is selected from the group consisting of cancers, tumors, malignancies, uncontrolled tissue or cellular proliferation secondary to tissue injury, polycystic kidney disease, inflammatory diseases and malaria.

142. The method of claim 133, wherein the disease condition is a cancer selected from the group consisting of hepatocellular carcinoma, liver metastases, cancers of the gastrointestinal tract, pancreas, prostate and lung, and Kaposi's sarcoma.

143. The method of claim 133, wherein the enhancing agent is orally administered in a separate oral dosage form.

144. The method of claim 67, wherein the subject is a human.

145. The method of claim 93, wherein the subject is a human.

146. The method of claim 96, wherein the subject is a human.

147. The method of claim 106, wherein the subject is a human.

148. The method of claim 109, wherein the subject is a human.

149. The method of claim 118, wherein the subject is a human.

150. The method of claim 133, wherein the subject is a human.

151. The method of claim 126, wherein the co-solubilizer further comprises ethanol.

152. The method of claim 93, wherein said composition is in an oral dosage form of a hard or soft gelatin capsule.

153. The composition of claim 60, wherein said co-solubilizer further comprises ethanol.

154. The method of claim 137, wherein the taxane is paclitaxel.

155. The method of claim 154, wherein the subject is a human.

156. The method of claim 137, wherein the taxane is docetaxel.

157. The method of claim 156, wherein the subject is a human.

158. The method of claim 138, wherein the taxane is paclitaxel.

159. The method of claim 158, wherein the subject is a human.

160. The method of claim 138, wherein the taxane is docetaxel.

161. The method of claim 160, wherein the subject is a human.

\* \* \* \* \*

UNITED STATES PATENT AND TRADEMARK OFFICE
CERTIFICATE OF CORRECTION

PATENT NO.    : 6,964,946 B1
DATED         : November 15, 2005
INVENTOR(S)   : Jose C. Gutierrez-Rocca et al.

It is certified that error appears in the above-identified patent and that said Letters Patent is hereby corrected as shown below:

Column 2,
Line 37, "dates" should read -- date, --.

Column 3,
Line 64, "provides" should read -- provide --.

Column 4,
Line 9, after "which" delete "10".

Column 5,
Line 56, "Hütis" should read -- Hüls --.
Line 63, after "as" delete "a".

Column 10,
Line 59, after "second" delete ",".

Column 14,
Line 41, immediately after "Table 4" insert -- *Not an actual HLB value of mixture. Numbers represent HLB values of pure surfactants. --.
Line 66, immediately after "Table 5" insert -- *Not an actual HLB value of mixture. Numbers represent HLB values of pure surfactants. --.

Column 19,
Line 55, "in" should read -- is --.

Column 22,
Line 27, "$C_8$-$C_{10}$" should read -- C8-C10 --.
Line 36, "500%" should read -- 50% --.

UNITED STATES PATENT AND TRADEMARK OFFICE
CERTIFICATE OF CORRECTION

PATENT NO. : 6,964,946 B1
DATED : November 15, 2005
INVENTOR(S) : Jose C. Gutierrez-Rocca et al.

It is certified that error appears in the above-identified patent and that said Letters Patent is hereby corrected as shown below:

Column 25,
Lines 1, 15 and 17, "palm kernel" should read -- palmkernel --.
Line 22, "$C_8$-$C_{18}$" should read -- C8-C18 --.

Signed and Sealed this

Seventh Day of March, 2006

JON W. DUDAS
*Director of the United States Patent and Trademark Office*